United States Patent [19]

Antonevich

[11] Patent Number: 4,558,309

[45] Date of Patent: Dec. 10, 1985

[54] GROUND TETHER CONTINUITY MONITOR

[75] Inventor: John N. Antonevich, Lansdale, Pa.

[73] Assignee: The Simco Company, Inc., Hatfield, Pa.

[21] Appl. No.: 507,977

[22] Filed: Jun. 27, 1983

[51] Int. Cl.$^4$ .......................................... G01R 31/02
[52] U.S. Cl. ................................... 340/649; 324/51; 340/573; 340/652; 340/658; 361/42
[58] Field of Search .............. 340/649, 652, 506, 507, 340/510, 573, 658, 568, 565, 660; 361/42; 324/51 (US only); 128/734; 331/64, 65; 174/5 R, 5 SB, 5 SG, 6

[56] References Cited

U.S. PATENT DOCUMENTS

| | | | |
|---|---|---|---|
| 2,611,862 | 9/1952 | Riddle et al. | 340/649 X |
| 3,040,211 | 6/1962 | Caldwell | 340/649 X |
| 3,290,668 | 12/1966 | Perretta | 340/649 |
| 3,343,154 | 9/1967 | Seesselberg | 340/649 |
| 3,450,947 | 6/1969 | Rogers, Sr. | 340/649 X |
| 3,452,346 | 6/1969 | Kupersmit | 340/565 X |
| 3,462,755 | 8/1969 | Hansen | 340/507 |
| 3,492,567 | 1/1970 | Rissolo | 361/42 X |
| 3,755,688 | 8/1973 | Hohler | 340/652 X |
| 3,878,459 | 4/1975 | Hanna | 340/660 X |
| 4,187,504 | 2/1980 | Cantrell | 340/652 |
| 4,188,574 | 2/1980 | Allington | 324/51 |
| 4,220,951 | 9/1980 | Bash et al. | 340/649 |
| 4,225,899 | 9/1980 | Sotiriou | 340/652 X |
| 4,293,852 | 10/1981 | Rogers | 340/568 |
| 4,295,132 | 10/1981 | Burney et al. | 340/568 X |

Primary Examiner—James L. Rowland
Assistant Examiner—Thomas J. Mullen, Jr.
Attorney, Agent, or Firm—Stanley Bilker

[57] ABSTRACT

A monitor for sensing any break in electrical continuity between a body and earth when the body is coupled to earth by way of a grounding tether used to prevent build-up of static charges on such body. The monitor includes an oscillator circuit for generating A.C. output voltages which are adapted to actuate an alarm. Body capacitance and resistance are coupled by way of the tether across an impedance network either in the tuned circuit determining oscillator frequency or in the output load thereof whereby the resistance or inductance of the impedance network provides the path to ground for the body through its tether. With body capacitance and resistance components of the total impedance, variable elements in the impedance network are adjusted to diminish the circuit output voltage below the threshold voltage required to actuate the alarm when continuity exists while developing an output voltage level sufficient to actuate the alarm when a break in continuity occurs.

20 Claims, 4 Drawing Figures

GROUND TETHER CONTINUITY MONITOR

BACKGROUND OF THE INVENTION (a) Field of the Invention

This invention relates to electrically conductive grounding straps or tethers which are attached to the body by way of the individual's arms, legs or clothing in order to ground operating personnel and prevent build-up of static charges on such persons. More particularly, this invention pertains to a monitoring system for insuring that electrical continuity exists between such persons and ground with means for sounding an alarm and/or providing a visual signal whenever an open circuit or break is detected between the human body and the tether to earth. This invention is especially concerned with the use of oscillator circuitry for generating A.C. output voltages adapted to actuate an alarm in combination with an impedance network (either in the tuned circuit of the oscillator or in the load circuit thereof) to which the distal end of the tether is connected and which provides a path to ground for the body through the resistance or inductance of such impedance. The monitor of the present invention incoporates body capacitance and resistance as components of the impedance network. By way of adjustable elements in the circuit's impedance network, the impedance can be varied so that the A.C. output voltage of the circuit may be reduced below a level which will actuate the alarm when continuity exists but when a break in continuity occurs, the output voltage will exceed the threshold level of the alarm or its input circuit and trigger the alarm.

(b) Prior Art

During the handling of sensitive electronic parts and equipment, it is essential that the electrical voltage between operating or handling personnel and the electronic objects be maintained at a minimum so as to avoid destructive breakdown of voltage sensitive components. To protect against electrical energy flow between the handler and the object being handled, every effort is made to maintain both the personnel and the electronic components at ground potential by means of electrically conductive grounding systems. These grounding systems drain off charges that might otherwise build up by charge transfer or by frictional or triboelectric forces or as a result of exposure within an electrical field. Such grounding devices commonly consist of electrically conductive straps or tethers, one end of which is tied to an arm, leg or body of the user or to conductive articles of clothing while the distal end is attached to earth usually by means of a clip or terminal via a grounded water pipe or electrical cable.

One problem which has arisen in the past occurred as a result of an unperceived open circuit or break between the tether wearer and his conductive path to earth, most frequently when the terminal clip of the tether became accidentally dislodged from its grounding post but on occasion because of discontinuity at the proximal contact end or from defects in the strap itself. Under such circumstances, the human body, no longer now being discharged through the grounding tether and representing a capacitance of perhaps 50 to 250 picofarads with respect to earth, could easily develop without his awareness a potential of up to 25,000 volts, for example.

A person so charged, but believing that charge drain-off was continuing via the tether, could during discharge cause destruction of the electronic component by dielectric breakdown or detonate an explosive environment by generating a spark.

It is therefore an object of this invention to provide in combination with an electrically conductive ground tether a monitor for detecting any open circuit or break in electrical continuity between the tether wearer and ground.

Another object of this invention is to provide a sensing apparatus for continuously monitoring ground tether continuity.

Yet another object of this invention is to provide a monitoring circuit for coupling a human body to earth through his grounding tether wherein an alarm signal will be actuated in the event of a break in electrical continuity between the tether wearer and his path to ground.

Yet still another object of this invention is to provide a ground tether fault detector employing oscillator circuitry in which body capacitance and resistance forms part of a variable impedance network whereby adjustment of the total impedance will diminish the A.C. voltage output when continuity exists to a level below that sufficient to actuate an alarm but when a break in continuity from the body to ground occurs will cause the A.C. output level to exceed the threshold necessary to trigger said alarm.

Other objects of this invention is to provide an improved device of the character described which is easily and economically produced, sturdy in construction and highly efficient and effective in operation.

SUMMARY OF THE INVENTION

In accordance with the present invention, there is provided a monitor for detecting any break in electrical continuity of the conductive path coupling a body to earth by way of a grounding tether. The monitor employs an oscillator circuit and associated amplification means whose A.C. output is adapted to actuate an alarm. The oscillator circuit includes an impedance network for receiving the distal end of the tether, which impedance through an inductive or resistive element thereof provides an extension of the tethered path to ground from the body. The impedance network of this invention may either be part of the tuned circuit which determines the oscillator frequency or form part of the load of the amplified output in connection with the alarm circuitry. By coupling the tether to the impedance network, the body capacitance and resistance become components of the impedance network and part of the active circuitry such that the A.C. output will depend upon whether the tether ties the body to ground through the impedance network (condition of continuity) or whether a break has occurred in the conductive path from the body (open circuit condition). The various elements of the impedance network are selected so that the A.C. output of the monitoring circuit, with the body capacitance and resistance removed, match the operating requirements of the alarm circuitry. At least some of the elements of the impedance network are adjustable so that accommodation can be made for variations in body capacitance and resistance of different individuals. The variable elements of the impedance are adjustable manipulated during set up whereby the A.C. output voltage is reduced to a level below that which will actuate the alarm when continuity exists but which will provide an output voltage exceeding the threshold level of the alarm and effect actuation thereof should a break in continuity occur. The alarm can provide visual and/or audible indications to alert personnel of any open circuit.

BRIEF DESCRIPTION OF THE FIGURES

With the above and related objects in view, this invention consists of the details of construction and combination of parts as will be more fully understood from the following detailed description when read in conjunction with the accompanying drawing in which.

DETAILED DESCRIPTION OF PREFERRED EMBODIMENTS

Figure 1:
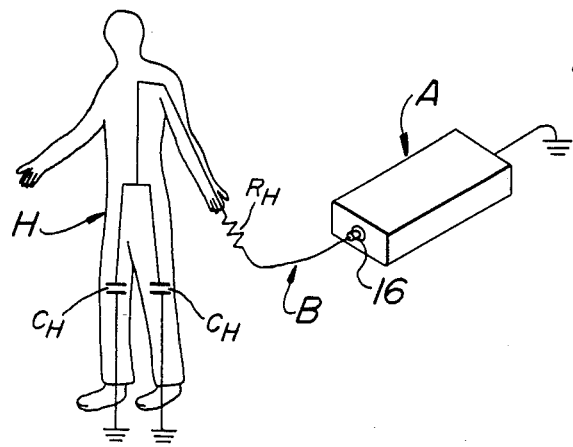
FIG. 1 is a perspective view, and partly schematic, of a ground tether continuity monitor embodying this invention.

Referring now in greater detail to the drawings in which similar reference characters refer to similar parts, I show a monitor A for detecting any break in electrical continuity of the conductive path between personnel H who are adapted to be coupled to earth by means of a ground tether B.

The grounding tether B is well known in the art and comprises any electrically conductive strap or lead, one end of which is proximally connected to the human body by way of the wrist, legs or through the wearer's clothing while the distal end of such tether is usually attached to electrical ground through a terminal on a water pipe or the neutral of an electrical cable. The tether B conventionally incorporates about one megohm of resistance to protect operating personnel by limiting current flow should a portion of the tether accidentally come into contact with a highly charged object or high voltage energy source.

The human body itself exhibits a capacitance $C_H$ ranging from about 50 to 250 picofarads with respect to earth depending upon the nature of the clothing being worn, whether the individual is standing or sitting and/or whether one or both feet are in contact with the floor. The resistance value $R_H$ of the human body including surface resistivity and contact resistance between the skin and the point of contact with the proximal end of the tether B is roughly 1,000 ohms. Thus, as shown in FIG. 1, the equivalent circuit for the body with respect to ground, when no tether exists or if the tether is disconnected from ground or if any break in continuity between the body and ground occurs, may be treated as a capacitor $C_H$ in series with a resistor $R_H$ and the tether resistance, if a tether resistance is incorporated.

Figure 2:
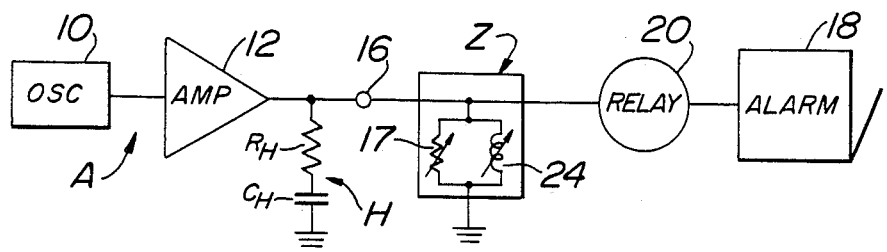
FIG. 2 is a block diagram, and partly schematic, showing one mode of the present invention.

Referring now to FIG. 2, the monitor A is shown by way of a general block diagram in which an oscillator 10 is coupled to an operational amplifier 12 whose A.C. output is developed across an impedance Z. The impedance Z preferably includes adjustable resistive or inductive elements which form an extension of the path to ground when the distal end of the tether B is connected to terminal or jack 16. An alarm 18 is either directly coupled to the A.C. output across the impedance Z (or indirectly by way of a relay 20) and is activated whenever the A.C. output voltage exceeds a predetermined level. The alarm 18 may be any suitable electronic, piezo electric or solid state sounding device, such as a series KMB miniature solid state buzzer, made by Star Micronics, Inc., of New York, N.Y., providing a minimum audible signal of about 85 db. The alarm 18 could also comprise a visual indicating device, such as a lamp or LED. The oscillator 10 also may be any conventional solid state or transistorized frequency generator which is capable in combination with the amplifier circuit 12 of providing an A.C. output voltage sufficient to actuate the alarm 20 (or the relay 18 for tripping the alarm).

When the free end of the tether B is connected across the load Z by way of the jack 16, the human equivalent $C_H + R_H$ would be made to appear as a low impedance across the output Z of the amplifier circuit 12 and through appropriate manipulation of the adjustable resistive or inductive elements therein, the capacitive-resistive body circuit can be made to squelch the activating circuit for the alarm 18. However, should a break in continuity occur anywhere between the body H and ground, the capacitance $C_H$ and the resistance $R_H$ will no longer shunt the load whereby the voltage output level at the load impedance Z will be sufficient to trip the alarm 18 (or its actuating relay 20).

Figure 3:
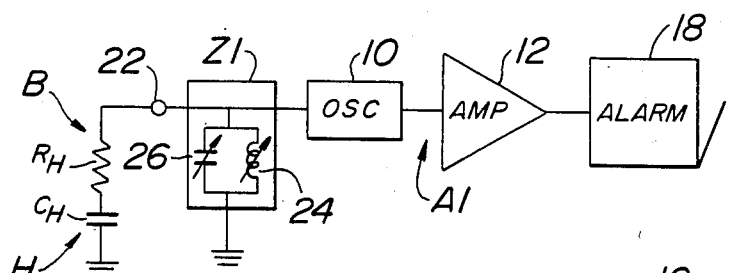
FIG. 3 is a block diagram, and partly schematic, showing another mode of the present invention.

Referring now to FIG. 3, the tether B (and the human body H with capacitance $C_H$ and resistance $R_H$) is coupled across the frequency determining element Z1 of the oscillator 10. The distal end of the tether B is connected to the terminal jack 22 of oscillator 10 such that the body H is grounded through variable choke coil 24 of impedance Z1. However, before tying the equivalent human circuit $C_H R_H$ across the frequency determining element constituting tank Z1, the output of the operational amplifier 12 is initially tuned by appropriate adjustment of variable choke 24 or variable capacitor 26 to match the frequency response of the alarm circuit 18, thus making certain that the alarm 18 does sound with the tether disconnected—i.e. alarm 18 is first test actuated. Then, with the tether B connected to jack 22, adjustment of the variable choke 24 or capacitor 26 is next performed with the $C_H$ and $R_H$ included as part of the tank circuit Z1 until sufficient detuning has been produced to deactivate the alarm 18. Now, when a break in the path to ground via the tether B occurs, the human capacitance and resistance will no longer be part of the tank circuit Z1 whereupon the A.C. output will cause the alarm to be actuated again.

Figure 4:
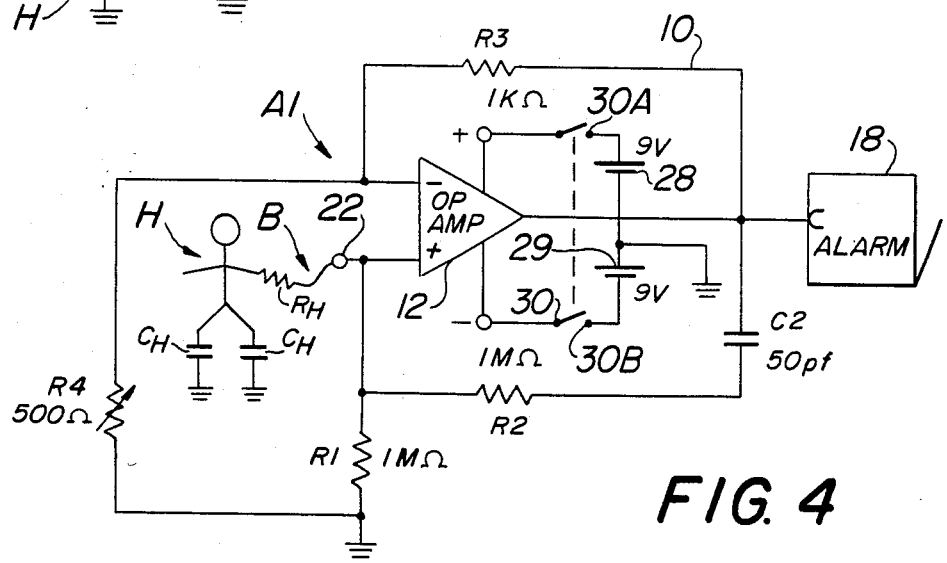
FIG. 4 is a schematic diagram showing circuitry for performing the mode of FIG. 3.

Referring now to FIG. 4, there is shown an example of the circuitry for performing the function set forth in the block diagram of FIG. 3. The monitor A1 incorporates a Wien bridge oscillator whose frequency is determined by a resistance capacitance network which provides regenerative coupling by way of feedback between the output and input of amplifier 12. The amplifier 12 may be any electronic or solid state design, such as Type SN72741 general purpose operational amplifier, sold by Texas Instruments, of Dallas, Tex. The oscillator bridge circuit includes resistors R1 and R2 which are equal to each other and selected to be about one megohm each to approximate the resistance of the tether B by itself. Resistor R3 is selected to be approximately 1,000 ohms or about twice that of the maximum value of the variable resistor R4. Capacitance C2 in series with resistor R2 is selected to be approximately 50 picofarads and compares with the 50 picofarad lower range capacitance of the human $C_H$. Piezo electric buzzer alarm 18 is connected to the output of the oscillator amplifier 12. The distal end of the tether B is connected to jack 22 whereby the body $C_H$ and $R_H$ is coupled across R1 which now forms the path to ground from the end of the tether and acts as part of the impedance Z1 defining the frequency determining network of the oscillator circuit. D.C. input supply voltages to the operational amplifier 12 are furnished, for example, by two 9 volt batteries 28 and 29 series connected with respect to each other and having the adjoined terminals grounded. Ganged ON-OFF switch 30 is adapted when closed to couple the positive terminal of battery 28 to the (+) input of operational amplifier 12 through contacts 30A and connect the negative terminal of battery 29 to the (−) input of said amplifier through contacts 30B.

In the configuration shown in FIG. 4, the oscillator circuit 10, with switch 30 closed but without the tether B attached, is first approximately tuned by means of variable resistor R4 to provide an A.C. voltage output from the amplifier 12 as will exceed the threshold level of the alarm circuit 18, thereby assuring that the alarm 18 does function. When the tether B is attached to the jack 22, the body capacitance $C_H$ is shunted to ground by way of resistor R1. Now, the variable resistor R4 is adjusted, if required, by backing said resistor R4 off sufficiently to provide an A.C. output just below the level for activating the alarm 18. Note that the feedback for the amplifier 12 by way of resistor R3 is controlled by variable resistor R4 to accommodate for any additional amount by which the human capacitance $C_H$ exceeds the bridge capacitance C2. Thus, should any break in continuity occur between the body H and its path to ground through impedance resistor R1, the output signal level from the amplifier 12 will exceed the threshold level of the alarm circuit 18 and cause activation thereof.

It is apparent from the foregoing description that the tying of the human equivalent across the impedance element of an active circuit, such as the resistive or inductive load of an oscillator-driven amplifier, as shown in FIG. 2, would modify the output impedance sufficiently as to squelch the amplifier output, thus providing an indication of continuity between the body and ground through the tether. When a break occurs, the shunt would be removed across the load so as to actuate the alarm. In the embodiment of FIGS. 3 and 4, tying the human equivalent circuit across the frequency determining impedance element of a critically tuned active circuit, such as an oscillator, and defining a path to ground through a choke or a resistor, would similarly deactivate the alarm, either by changing the output frequency or the A.C. output voltage level. Should an open circuit occur in the path from the body to ground, $C_H$ would be removed and the circuit would again be critically tuned so as to enable the alarm to be activated once more.

Although this invention has been described in considerable detail, such description is intended as being illustrative rather than limiting since the invention may be variously embodied without departing from the spirit thereof, and the scope of the invention is to be determined as claimed.

What is claimed is:

1. In combination with an electrically conductive tether for grounding a substantially non-conductive body to prevent build-up of static charges thereon, a monitor for detecting any break in electrical continuity between the body and ground, comprising:

frequency generator means for developing an A.C. output, alarm means coupled to the output of said frequency generator means, means associated with said frequency generator means and constituting an impedance network defining a frequency determining circuit therefor, said impedance network including a branch adapted to provide a continuous conductive path between said non-conductive body and ground when the tether is connected to the monitor, and means to couple the distal end of the body-attached tether to ground through said impedance network, said impedance network being so constructed and arranged that the A.C. output of said frequency generator means when continuity exists between the body and ground is insufficient to actuate said alarm means by virtue of body capacitance present at the proximal end of the tether and, when any break in continuity between the body and ground occurs, absence of body capacitance will so change the characteristics of the A.C. output that the alarm means will be actuated.

2. The monitor of claim 1 wherein said impedance network includes feedback means for said frequency generator means.

3. The monitor of claim 2 wherein said frequency generator means comprises an oscillator circuit.

4. The monitor of claim 3 wherein coupling the tether to the impedance network detunes said oscillator circuit when continuity exists between the body and ground.

5. The monitor of claim 1 including means to adjust the impedance network of said frequency determining circuit.

6. The monitor of claim 1 wherein said frequency determining means comprises a Wien bridge.

7. The monitor of claim 6 wherein one arm of the Wien bridge includes a variable resistor.

8. The monitor of claim 1 wherein said impedance network is part of the load of said frequency generator means.

9. The monitor of claim 8 wherein coupling the tether to the impedance network acts to squelch the load when continuity exists.

10. The monitor of claim 8 including relay means coupled to the A.C. output for actuating said alarm means.

11. A monitor for sensing any break in electrical path between a substantially non-conductive body and ground by way of a conductive tether, comprising:

alarm means for alerting personnel of an open circuit between the body and ground, frequency generator means adapted to develop an A.C. output sufficient to actuate said alarm means, circuit means constituting a frequency determining network for said frequency generator means, said circuit means including a branch adapted to provide a continuous conductive path between said non-conductive body and ground when the tether is connected to the monitor, and means for coupling the distal end of the body attached tether to ground through said frequency determining network so that body capacitance is introduced into said frequency determining network when continuity exists to effect oscillation of said frequency generator means at a level insufficient to actuate said alarm means, and when a break in continuity occurs between the body and ground, the absence of body capacitance will produce a change in the characteristics of the A.C. output above the level which will actuate said alarm means.

12. The monitor of claim 11 wherein the frequency determining network comprises an impedance.

13. The monitor of claim 12 wherein said impedance is adjustable.

14. The monitor of claim 12 wherein said frequency determining network comprises a Wien bridge.

15. The monitor of claim 14 wherein one arm of the Wien bridge includes an adjustable resistor.

16. A monitor for sensing any break in electrical path between a substantially non-conductive body and ground by way of a conductive tether, comprising:
 an alarm for alerting personnel of an open circuit between the non-conductive body and ground,
 an oscillator having an A.C. output coupled to said alarm,
 an impedance network defining a frequency determining circuit for said oscillator and including a branch adapted to provide a continuous conductive path between said nonconductive body and ground when the body-attached tether is connected to the monitor,
 said oscillator being so constructed and arranged in relation to said frequency determining circuit as to generate an oscillatory output insufficient to actuate said alarm when continuity exists between the body and ground through said impedance network, and, when any break in continuity occurs between the body and ground, the absence of body capacitance will produce a change in such oscillatory output as will cause actuation of said alarm.

17. The monitor of claim 16 wherein said impedance network includes a variable inductance.

18. The monitor of claim 16 wherein said impedance network includes adjustable components.

19. The monitor of claim 16 wherein said oscillator is of a Wien bridge configuration.

20. The monitor of claim 19 wherein one arm of the Wien bridge includes a variable resistor.

* * * * *